US012672948B2

(12) United States Patent
Vanoni et al.

(10) Patent No.: US 12,672,948 B2
(45) Date of Patent: Jul. 7, 2026

(54) IMPLANT CASE

(71) Applicant: Surgical Fusion Technologies GmbH, Schlieren (CH)

(72) Inventors: Michele Vanoni, Zürich (CH); Andrea Müller, Winterthur (CH); Manuel Kallen, Austrasse (CH)

(73) Assignee: SURGICAL FUSION TECHNOLOGIES GMBH, Schlieren (CH)

( * ) Notice: Subject to any disclaimer, the term of this patent is extended or adjusted under 35 U.S.C. 154(b) by 27 days.

(21) Appl. No.: 18/736,395

(22) Filed: Jun. 6, 2024

(65) Prior Publication Data

US 2025/0375283 A1     Dec. 11, 2025

(51) Int. Cl.
| | |
|---|---|
| *A61F 2/00* | (2006.01) |
| *A61B 17/04* | (2006.01) |
| *A61B 17/80* | (2006.01) |
| A61B 17/00 | (2006.01) |
| A61B 17/56 | (2006.01) |
| A61F 2/46 | (2006.01) |

(52) U.S. Cl.
CPC ........ *A61F 2/0095* (2013.01); *A61B 17/0482* (2013.01); *A61B 17/808* (2013.01); *A61B 2017/00955* (2013.01); *A61B 2017/0409* (2013.01); *A61B 2017/0416* (2013.01); *A61B 2017/564* (2013.01); *A61F 2002/4683* (2013.01)

(58) Field of Classification Search
CPC ............ A61B 17/04; A61B 2017/0409; A61B 2017/0414; A61B 2017/0416; A61B 17/0482; A61F 2/0095
See application file for complete search history.

(56) References Cited

U.S. PATENT DOCUMENTS

| | | | |
|---|---|---|---|
| 2,281,781 A | 5/1942 | Merrill et al. | |
| 5,715,942 A * | 2/1998 | Li ........................... | A61B 17/04 |
| | | | 206/339 |
| 5,814,069 A * | 9/1998 | Schulze ............... | A61B 17/062 |
| | | | 606/228 |
| 6,346,109 B1 * | 2/2002 | Fucci ................. | A61B 17/0469 |
| | | | 606/104 |
| 9,427,228 B2 * | 8/2016 | Hart ................. | A61B 17/06114 |
| 9,615,820 B2 * | 4/2017 | Mayer ................ | A61B 17/0401 |
| 2012/0095506 A1 | 4/2012 | Mayer et al. | |
| 2013/0325063 A1 | 12/2013 | Norton et al. | |
| 2022/0323198 A1 | 10/2022 | Zenz-olson et al. | |

FOREIGN PATENT DOCUMENTS

| | | |
|---|---|---|
| EP | 0 982 003 A2 | 3/2000 |
| EP | 0 982 003 A3 | 5/2001 |
| WO | 0002477 A2 | 1/2000 |
| WO | 2012/037699 A1 | 3/2012 |

OTHER PUBLICATIONS

International Search Report in related application No. PCT/EP2025/065750, mailed Sep. 15, 2025.

* cited by examiner

*Primary Examiner* — Larry E Waggle, Jr.
(74) *Attorney, Agent, or Firm* — Procopio, Cory, Hargreaves & Savitch LLP

(57) ABSTRACT

A device having a housing with specifically arranged openings for storing an implant, a kit of parts comprising the device as well as corresponding methods of assembly and implantation.

34 Claims, 5 Drawing Sheets

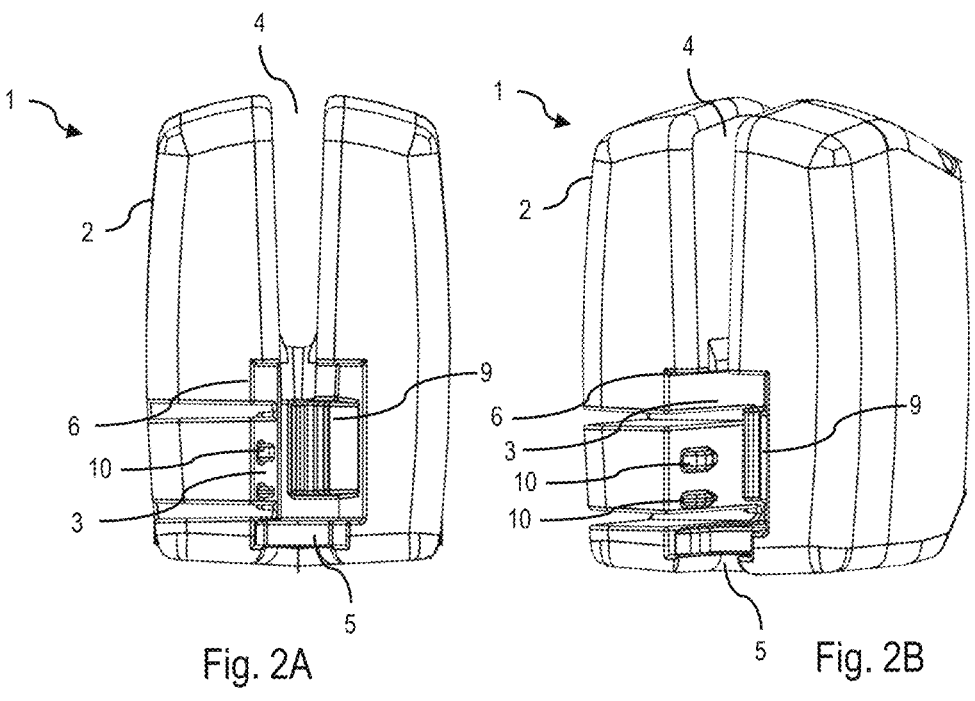
Fig. 2A                    Fig. 2B
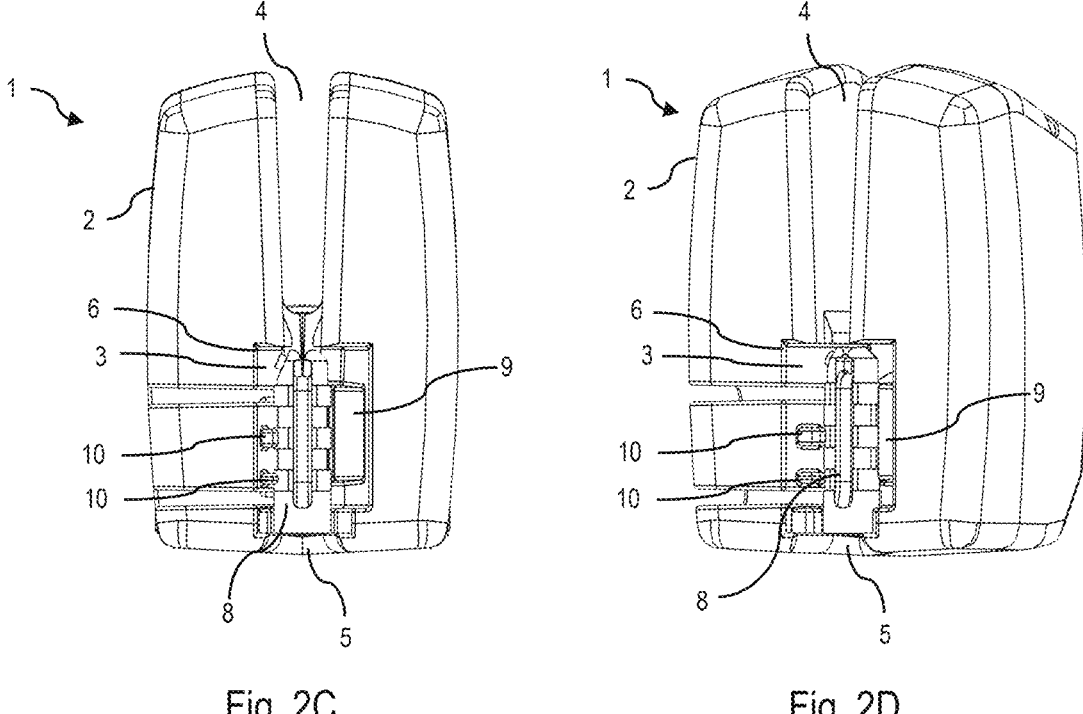
Fig. 2C                    Fig. 2D

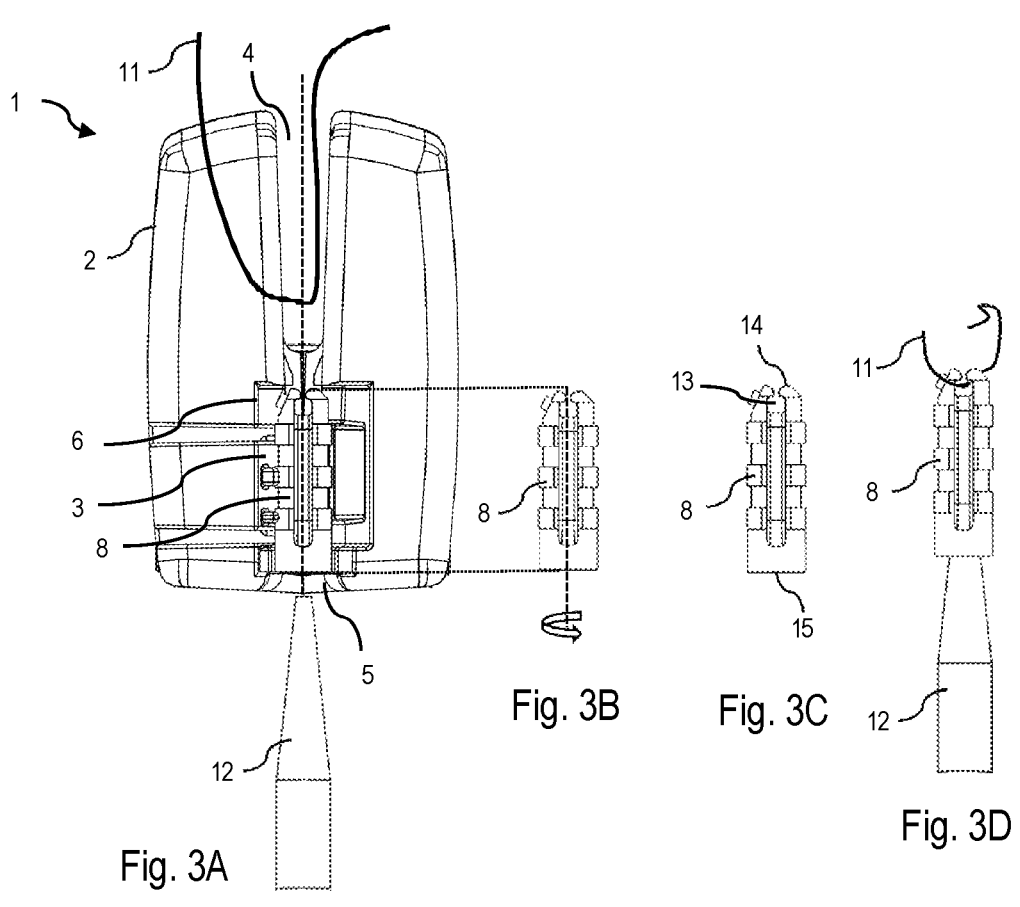
Fig. 3A
Fig. 3B
Fig. 3C
Fig. 3D
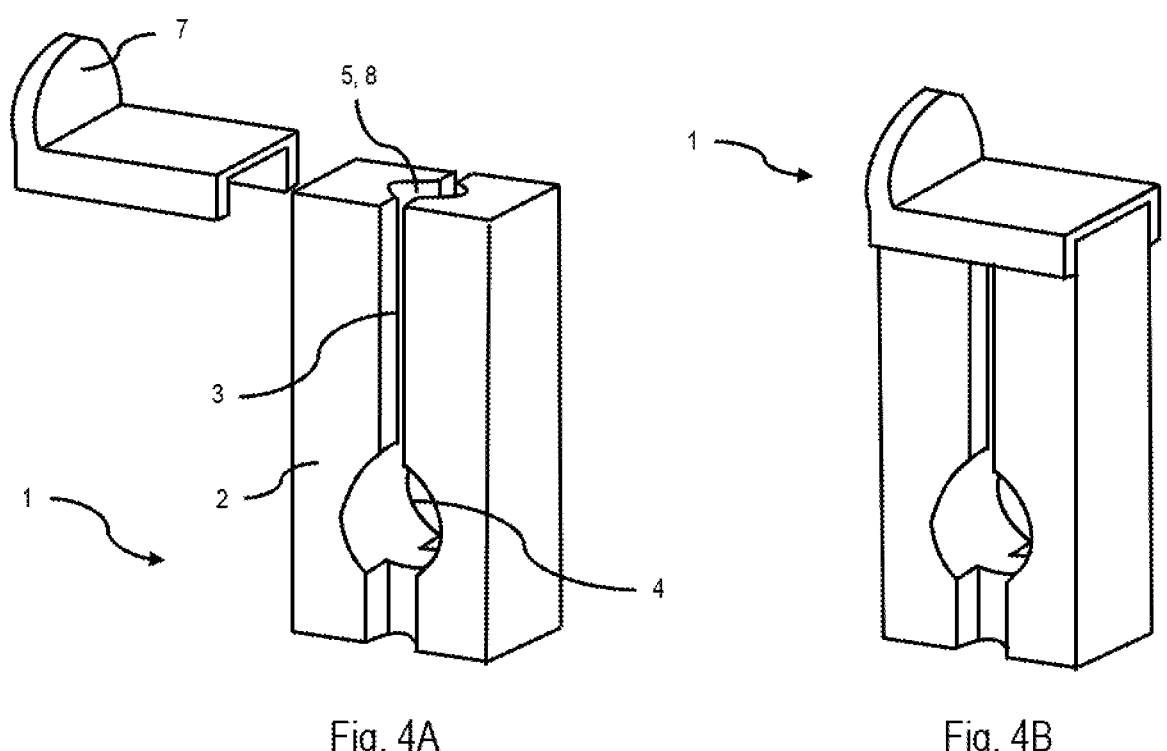
Fig. 4A
Fig. 4B

IMPLANT CASE

TECHNICAL FIELD OF THE INVENTION

The current invention relates to a device for storing an implant, a kit of parts comprising the device as well as corresponding methods of assembly and implantation.

DESCRIPTION OF THE RELATED ART

Known implant cases are typically built in the form of racks which comprise multiple implants or require a user to touch the implant for further manipulation.

SUMMARY OF THE INVENTION

It is a task of current invention to provide an improved implant case which protects the implant and facilitates handling thereof.

This task is solved by a device, kit of parts and methods with the features of claims 1 to 4, 20, 23 and 28. Further embodiments of the device, kit of parts and methods are defined by the features of further claims.

In a first aspect, the present invention is directed to a device for storing an implant comprising a housing defining a cavity suitable for receiving and storing an implant of a predefined geometry, wherein the housing comprises:

a top opening for guiding a suture to an implant stored in the cavity, optionally for attaching a suture to an implant stored in the cavity, a bottom opening for attaching a sonotrode to an implant stored in the cavity, and a side opening for inserting an implant into the cavity and for extracting an implant, in particular an implant attached to a sonotrode, in particular attached to the sonotrode via the bottom opening, from the cavity, wherein the cavity is located between the top and bottom openings, the housing is configured to position an implant having said predefined geometry in the cavity such that a suture can be guided to or from the implant, optionally attached to the implant, via the top opening and a sonotrode can be attached via the bottom opening to the implant, and the top and bottom openings are positioned essentially opposite each other and are configured such that an implant having said predefined geometry cannot pass through the top opening and cannot pass through the bottom opening.

The present device allows for the protection of an implant by storing the same in the device, while the device facilitates, e.g., the extraction of the implant and the guidance (e.g. insertion) of a suture into or from the implant. Furthermore, the device allows the handling of the implant without (manually) touching it.

The housing defines a cavity which means that the housing comprises a cavity that is formed by the structure of the housing. The housing defines a cavity suitable for receiving and storing an implant, which means that the cavity is shaped by the housing such that it is suitable, e.g., for reversibly fixating the implant in the housing such that it does not fall out but can be extracted by an operator, e.g. with a sonotrode, in particular without touching the implant by hand when extracting the same. The storing further includes that the housing, in particular around the cavity, is configured to position an implant having the predefined geometry in the cavity such that a suture can be guided to or from the implant, e.g. attached to the implant, via the top opening and a sonotrode can be attached via the bottom opening to the implant. In other words, the housing, in particular around the cavity, allocates the relevant sites (those for suture guidance and/or attachment and sonotrode attachment) of the implant to the top and bottom openings. The storing may further include orienting the implant in a predetermined way in the cavity, e.g. based on the implant's geometry. The implant may feature a specific shape that is used in combination with a shape of the cavity to orient the implant, e.g. around a longitudinal axis of an elongated implant or around an axis perpendicular to the longitudinal axis.

The predefined geometry of the implant includes the shape and size of the implant. Implants, as referred to herein, are medical devices, in particular orthopedic implants, e.g. implants that are implanted into hard tissue such as bones, including pins, rods, screws, and (suture) anchors. These implants have, due to their intended applications, a limited size range. Exemplary size ranges are detailed further below.

Due to the limited size range of implants, the skilled person can routinely determine whether a device has a housing according to the present invention. The top and bottom openings are configured such that an implant having said predefined geometry cannot pass through the top opening and cannot pass through the bottom opening. This can be achieved, e.g., by defining the opening area of the openings to be smaller than the smallest cross-section of the implant, or by suitable means at or near the openings which prevent the passage of the implant through the openings. Suitable means include, e.g., closing means or structural means (e.g. notches) which extend into the openings and prevent implant from passing through.

The top and bottom openings are positioned essentially opposite each other and the cavity is located between the openings. In other words, the top and bottom openings are connected to the cavity (i.e. they from a passage to the cavity through the housing) such that a suture can be guided to or from the implant, e.g. attached to the implant, via the top opening and a sonotrode can be attached via the bottom opening to the implant. The words "top" and "bottom" are to be understood as relative terms, in particular relative to the cavity since they are positioned essentially opposite each other with the cavity in between.

The side opening is suitable and/or configured for inserting an implant into the cavity and for extracting an implant attached to a sonotrode via the bottom opening, from the cavity. The side opening together with the housing and the bottom opening is configured such that the implant (e.g. without being attached to any further structure) can be inserted into the cavity and extracted from the cavity while being attached to a sonotrode that was attached to the implant via the bottom opening. Hence, the bottom and side opening are functionally connected. "Functionally connected" in the context of the bottom and side opening means that the openings are connected such that the implant can be extracted from the cavity via the side opening while being attached to a sonotrode that was attached to the implant via the bottom opening. The connection between the openings may, e.g., be structural in that the side opening and bottom opening are connected and form a continuous passage.

For example, the side opening extends into the housing towards the bottom opening or the bottom opening extends into the housing towards the side opening, allowing for the implant attached to the sonotrode to be extracted from the cavity. In this example, the bottom opening can, e.g., have the form of a slot, e.g. with at least the width of the sonotrode, through which slot the sonotrode can slide when extracting the implant attached to the sonotrode from the cavity in the housing. The slot can, e.g., be an incision into the housing. The functional connection also includes that the bottom and side openings are at least partially separated by structural means which do not hinder the extraction of the implant from the cavity when attached to the sonotrode, e.g. structural means that are resilient or flexible.

For example, the top opening can have a diameter of 0.1 mm to 7 mm, or an opening area of 0.2 mm² to 50 mm². For example, the bottom opening can have a diameter of 0.5 mm to 10 mm, or an opening area of 0.2 mm² to 60 mm². For example, the side opening can have a diameter of 1 mm to 30 mm, or an opening area of 2 mm² to 1'500 mm². For non-circular openings, the diameter refers to the largest distance in the opening.

For example, the cavity can have a volume of 1 mm³ to 25'000 mm³, optionally 2 mm³ to 15'000 mm³. For example, the cavity can have a length of 1 mm to 20 mm, a width of 1 mm to 20 mm and/or a height (direction bottom opening to top opening) of 2 mm to 80 mm.

The housing and the top opening are configured such that a suture can be guided to or from an implant in the cavity via the top opening from outside the housing. The guiding includes, e.g. attaching a suture to the implant and/or guiding a suture attached to the implant from the implant stored in the cavity via the top opening, e.g. along an outside surface or groove of the device. For example, the implant may already comprise a suture attached to it when it is inserted into the device; then, the top opening can serve to guide the suture of the inserted implant, e.g. in an orderly fashion, e.g. along suitable outside surface, e.g. a groove in the device, e.g. by interacting with the physical shape of the device. For example, a suture can be attached to the implant via the top opening, e.g., by hand, i.e. by manually attaching a suture from outside the housing to an implant inside the cavity, e.g. without the need for any instrumentation apart from, e.g., a needle. Relatively speaking, the cavity is located "inside" the housing, and the outside refers to the space around the housing.

For example, the device and the housing may be of a plastic material, in particular a thermoplastic material, that may be reinforced with glassfiber or carbonfiber, and/or that may be non-resorbable, sterilizable, and/or biocompatible. In particular, the housing may be of a plastic material that is formstable (e.g. has a glass-transition temperature Tg of more than 60° C.). Exemplary materials include polyethylene, PET, PVC, polypropylene, polyamide or a metal, e.g. stainless steel, titanium, or a ceramic material, or a biodegradable polymer.

In a second aspect, the present invention is directed to a device for storing an implant comprising an outer housing and a removable inner housing, wherein the outer housing comprises:

an outer top opening for guiding a suture to or from an implant stored in the inner housing, optionally for attaching a suture to an implant stored in the inner housing, an outer bottom opening for attaching a sonotrode to an implant stored in the inner housing, and at least one outer side opening, optionally for inserting and extracting the inner housing, and the inner housing, wherein the inner housing defines a cavity suitable for receiving and storing an implant of a predefined geometry, and comprises:

an inner top opening functionally connected to the outer top opening, an inner bottom opening functionally connected to the outer bottom opening, and an inner side opening functionally connected to the at least one outer side opening, and optionally further connected to the inner and outer bottom openings, for inserting an implant into the cavity and for extracting an implant, in particular an implant attached to a sonotrode, in particular attached to the sonotrode via the inner and outer bottom opening, from the cavity, wherein the cavity is located between the inner top and inner bottom openings, the inner housing is configured to position an implant having said predefined geometry in the cavity such that a suture can be guided to or from the implant, optionally attached to the implant, via the outer and inner top opening and a sonotrode can be attached via the outer and inner bottom opening to the implant, and the inner top and inner bottom openings, and the outer top and outer bottom openings are positioned essentially opposite each other and are configured such that an implant having said predefined geometry cannot pass through at least one of the inner top opening, the outer top opening, or both, and cannot pass through at least one of the inner bottom opening, the outer bottom opening, or both.

The definitions and explanations provided above in the context of the first aspect apply to the second aspect unless contradictory or specifically stated otherwise.

The housing, as defined in the first aspect, comprises an inner and an outer housing in the second aspect. In other words, the inner and outer housings of the second aspect together form the housing of the first aspect, with the differences in their features defined herein. In the second aspect, it is the inner housing that defines the cavity which is defined by the housing of the first aspect. Hence, all exemplary dimensions provided for the cavity of the first aspect apply to the cavity of the second aspect.

The outer housing and inner housing are shaped complementarily such that the inner housing can be reversibly positioned within the outer housing. The inner housing is thus removable from and re-insertable into the outer housing. Removable means that the inner housing can be reversibly removed and re-inserted, e.g. by a plug-fit connection. All definitions and explanations provided for the second aspect, unless contradictory or specifically stated otherwise, refer to the device, wherein the inner housing is inserted into the outer housing.

The inner and outer housings both have top and bottom openings, wherein the top openings and the bottom openings align respectively for guiding, optionally attaching, a suture and for attaching a sonotrode from outside the outer housing to an implant stored in the cavity of the inner housing. In other words, the top openings and the bottom openings, respectively, are functionally connected, wherein functionally means that the connection allows for guiding (e.g. attaching) a suture and attaching a sonotrode from the outside of the outer housing to an implant stored in the cavity of the inner housing.

The inner side opening and the at least one outer side opening align with each other such that they are functionally connected to allow at least for the insertion of the implant from outside the outer housing into the cavity of the inner housing. For example, the at least one outer side opening can be suitable for and/or configured such that the inner housing can be inserted into the outer housing via the at least one outer side opening. The outer housing may comprise further side openings, e.g. multiple side openings, which can be suitable for and/or configured to remove and insert the inner housing into the outer housing.

The explanations provided above in the context of the first aspect relating to the functional connection of the side and bottom openings apply mutatis mutandis to the second aspect in that the at least one outer side opening and the inner side opening and the inner and outer bottom openings are functionally connected, i.e. configured such that the implant (e.g. without being attached to any further structure) can be inserted into the cavity and extracted from the cavity via the at least one outer side opening and the inner side opening while being attached to a sonotrode that was attached to the implant via the inner and outer bottom openings.

The definitions and examples for the relative dimensions of the openings versus the implant provided for the first aspect of the present invention apply mutatis mutandis to the inner and outer openings of the second aspect. Hence, the exemplary dimensions and definitions for the top opening apply to the inner and/or outer top openings and the exemplary dimensions and definitions for the bottom opening apply to the inner and/or outer bottom openings.

It is sufficient for the device of the present invention that at least one of the inner and outer top openings and at least one of the inner and outer bottom openings is configured such that the implant having said predefined geometry cannot pass through. In other words, and for example, the outer top or bottom opening could be configured such that the implant could pass through while the inner top or bottom opening is configured such that the implant cannot pass through.

In a third aspect, the present invention is directed to a device for storing an implant comprising a housing defining a cavity suitable for receiving and storing an implant of a predefined geometry, wherein the housing comprises:

a top opening for guiding a suture to or from an implant stored in the cavity, optionally for attaching a suture to an implant stored in the cavity, a bottom opening for inserting and extracting an implant of a predefined geometry, and for attaching a sonotrode to an implant stored in the cavity, and closing means for closing the bottom opening, wherein the cavity is located between the top and bottom openings, the housing is configured to position an implant having said predefined geometry in the cavity such that a suture can be guided to or from the implant, optionally attached to the implant, via the top opening and a sonotrode can be attached via the bottom opening to the implant, the top and bottom openings are positioned essentially opposite each other, and the top opening is configured such that an implant having said predefined geometry cannot pass through the top opening.

The definitions and explanations provided above in the context of the first aspect apply to the third aspect unless contradictory or specifically stated otherwise.

In the third embodiment, and in contrast to the first and second embodiment, the bottom opening is configured to allow the implant to pass, in particular when attached to a sonotrode.

The device of the third aspect has a bottom opening for both, inserting and extracting the implant and for attaching a sonotrode. However, it is within the purview of the present invention that the "roles" of the bottom and top opening are reversed in that the bottom opening is for guiding (e.g. attaching) a suture to an implant stored in the cavity and the top opening is for inserting and extracting the implant and for attaching a sonotrode to the implant in the cavity. The housing of the third (and fourth) aspect may further, optionally, comprise one or more side openings (outer and/or inner side openings), as long as these side openings are configured such that the implant having said predefined geometry cannot pass through the side opening(s).

The closing means can any means that at least partially close the bottom opening, e.g. to the extent that the implant having said predefined geometry cannot pass through the bottom opening.

In a fourth aspect, the present invention is directed to a device for storing an implant comprising an outer housing and a removable inner housing, wherein the outer housing comprises:

an outer top opening for guiding a suture to or from an implant stored in the inner housing, optionally for attaching a suture to or from an implant stored in the inner housing, an outer bottom opening for inserting and extracting the inner housing, and for attaching a sonotrode to an implant stored in the inner housing, closing means for closing the outer bottom opening, and the inner housing, wherein the inner housing defines a cavity suitable for receiving and storing an implant of a predefined geometry, and comprises:

an inner top opening functionally connected to the outer top opening, an inner bottom opening functionally connected to the outer bottom opening, wherein the cavity is located between the inner top and inner bottom openings, the inner housing is configured to position an implant having said predefined geometry in the cavity such that a suture can be guided to or from the implant, optionally attached to the implant, via the outer and inner top opening and a sonotrode can be attached via the outer and inner bottom opening to the implant, and the inner top and inner bottom openings are positioned essentially opposite each other, and at least one of the inner top opening, the outer top opening, or both, is configured such that an implant having said predefined geometry cannot pass through at least one of the inner top opening, the outer top opening, or both.

The definitions and explanations provided above in the context of the first, second and third aspect apply to the fourth aspect unless contradictory or specifically stated otherwise. In particular, for the relationship between the inner and outer housings, as well as their comparison to the housing, reference is made to the definitions and explanations provided in the context of the second aspect of the present invention.

In an embodiment of the device according to the present invention, which may be combined with any of the aspects and embodiments of the device preaddressed or still to be addressed unless in contradiction, the housing or inner housing comprises at least one of:

means for retaining the implant in the cavity, means for positioning an implant in the cavity in a predetermined position, or both.

The predetermined position can be any position that allows for the attachment of a suture and a sonotrode via the respective openings. For example, the implant may feature a specific shape or structural feature that is used in combination with a shape of the housing around the cavity to position the implant, e.g. to align the implant. For example, the implant may have a structural feature that can be used to determine the position of a suture conduit in the implant relative to the top opening in order to facilitate the attachment of a suture in the suture conduit via the top opening or inner and outer top openings. Also, the predetermined position of the implant may refer to an alignment of an implant that is for use with a non-rotationally symmetrical sonotrode. For example, the implant may be oriented within the cavity such that the operator using a non-rotationally symmetrical sonotrode can attach the sonotrode without testing different orientations of the sonotrode because the cavity-implant interaction predetermines how the recess in the implant that receives the non-rotationally symmetrical sonotrode is oriented.

In an embodiment of the device according to the present invention, which may be combined with any of the aspects and embodiments of the device preaddressed or still to be addressed unless in contradiction, at least one of the means for retaining the implant in the cavity, the means for positioning the implant in the cavity, or both, extend into the cavity.

The means for retaining the implant in the cavity are attached to or part of the housing or inner housing and extend into the cavity. For example, these means can interact with the specific shape or structural feature of the implant to position the implant in the cavity. Alternatively, the means for retaining the implant in the cavity can be recesses in the housing which recesses can interact with the specific shape or structural feature of the implant to position the implant in the cavity.

In an embodiment of the device according to the present invention, which may be combined with any of the aspects and embodiments of the device preaddressed or still to be addressed unless in contradiction, at least one of the means for retaining the implant in the cavity, the means for positioning the implant in the cavity, or both, are clamping means for retaining the implant in the cavity.

The clamping means can, for example, be resilient parts, e.g. notches, of the housing or additional resilient means that interact with the implant.

In an embodiment of the device according to the present invention, which may be combined with any of the aspects and embodiments of the device preaddressed or still to be addressed unless in contradiction, the top opening is a slot or a funnel or the inner and outer top openings are a slot or a funnel.

The opening in the form of a slot can, for example, facilitate the guiding (e.g. attachment) of a suture to or from the implant in the cavity in that the suture can be aligned along the slot and pressed down to reach the implant for attachment. The slot is particularly useful if the implant is a suture anchor having a groove for guiding (e.g. attaching) a suture, wherein the suture is pressed into the groove via the slot (in particular when the device is configured such that the groove of the implant is aligned due to the shape of the cavity/housing (inner housing) with the slot). Also, the slot can serve to guide the attached suture along the device in an orderly fashion. The opening in the form of a funnel can, for example, facilitate the attachment of a suture to an implant that has an eyelet for receiving the suture. In this example, the device can be configured such that the funnel is aligned with the eyelet of the implant to direct a suture towards and optionally through the eyelet.

In an embodiment of the device according to the present invention, which may be combined with any of the aspects and embodiments of the device preaddressed or still to be addressed unless in contradiction, the housing or inner housing comprises means for positioning an implant in the cavity such that a suture conduit in the implant aligns with the slot or funnel in the top of the housing or in the inner and outer top openings, and that a suture can be guided from the suture conduit or inserted into the suture conduit via the slot or funnel. "Guided from the suture conduit" means, e.g., that the suture is guided from the implant's suture conduit via the slot or funnel to the outside of the device, e.g. to assure an ordered allocation of the suture.

The suture conduit can be a groove, channel or eyelet.

In an embodiment of the device according to the present invention, which may be combined with any of the aspects and embodiments of the device preaddressed or still to be addressed unless in contradiction, the device further comprises attachment means on the device or on the housing or outer housing for attaching the device to a sonotrode apparatus.

For example, the attachment means allow for the device to be attached to a sonotrode which can facilitate the handling of the implant and optionally a suture in surgery. For example, once the implant is extracted from the device, the device can be attached to a sonotrode and a suture attached to the implant can be guided and/or fixated by the device attached to the sonotrode, e.g. by mounting means such as conduits or clamping means in the device. For example, the attachment means can allow for the device to be attached to a handheld of a sonotrode.

In an embodiment of the device according to the present invention, which may be combined with any of the aspects and embodiments of the device preaddressed or still to be addressed unless in contradiction, the attachment means further comprise at least one of: mounting means for a needle, mounting means for a suture, or both.

In an embodiment of the device according to the present invention, which may be combined with any of the aspects and embodiments of the device preaddressed or still to be addressed unless in contradiction, the top and bottom openings or the inner top and inner bottom openings are dimensioned such that an implant having said predefined geometry cannot pass through the top opening or the bottom opening, or through the inner top or inner bottom opening, or the top and bottom openings, or at least one of the inner top and bottom openings, the outer top and bottom openings, or both, comprise means for preventing an implant having said predefined geometry to pass through the top opening or the bottom opening or through at least one of the inner top or bottom opening, the outer top or bottom opening, or both.

As explained above, the means for preventing the implant having said predefined geometry to pass through openings can be closing means or means that reduce the dimensions of the openings to the extent that the implant cannot pass.

In an embodiment of the device according to the present invention, which may be combined with any of the aspects and embodiments of the device preaddressed or still to be addressed unless in contradiction, the device comprises an implant of a predefined geometry, in particular an implant having a distal end and a proximal end, in the cavity.

The following definitions and examples for the implant are applicable to all aspects and embodiments disclosed herein. The implant has a specific geometry, i.e. a predefined geometry, which means that the implant has a specific shape and size for which the housing (or inner housing) and cavity of the device is configured such that the implant can be received, stored, positioned and extracted in the cavity of the device. The implant can be, e.g., a suture anchor as described herein.

As noted above, the implant is a medical device, in particular an orthopedic implant, e.g. an implant that can be implanted into hard tissue such as bones, including pins, rods, screws, and (suture) anchors. The implant can have any form or shape as long as it is suitable for being inserted and fixated in a recess of an object, in particular a hard tissue (bone), in a medical context. For example, the implant referred to in here has a cavity, recess, opening (which terms are used interchangeably) or elongated cavity, recess, opening or hole which can interact with a sonotrode so that the implant can be received and extracted from the cavity by the sonotrode. For example, the implant as described herein for all aspects and embodiments can be a suture anchor or pin that has an overall cylindrical shape, for example the shape of a dowel with a distal and a proximal end. For example, the cavity, recess, opening or elongated cavity for interaction with a sonotrode is positioned at a proximal end of the implant and/or a suture conduit (e.g. a groove, channel or eyelet) is positioned at the distal end of the implant. For example, the implant is stored and positioned in the device such that the distal end faces the top opening (or inner top opening) and the proximal end faces the bottom opening (or inner bottom opening).

For example, the implant may have a length of 2 mm to 80 mm, an outer diameter of 1 mm to 15 mm, and optionally with a cavity that stretches from the proximal end into the suture anchor towards the distal end over 0.5 mm to 10 mm and/or having a cavity diameter of 0.2 mm to 10 mm.

For example, the implant may be a suture anchor with an essentially cylindrical structure with a length of 4 mm to 20 mm, an outer diameter of 1 mm to 9 mm, and optionally with a cavity that stretches from the proximal end into the suture anchor towards the distal end over 0.5 mm to 8 mm and/or having a cavity diameter of 0.2 mm to 8 mm. The cavity may be cylindrical or polygonal (prismatic) and/or have a tapered (conus) shape (with the largest diameter at the proximal end of the suture anchor). For example, the implant may be a pin with the same dimensions as the anchor or with the following dimensions: length of 4 mm to 60 mm, outer diameter of 1 mm to 10 mm, cavity depth (from the proximal end into the pin towards the distal end) of 0.5 mm to 10 mm, and/or cavity diameter 0.2 mm to 8 mm.

In an embodiment of the device according to the present invention, which may be combined with any of the aspects and embodiments of the device preaddressed or still to be addressed unless in contradiction, the implant is an implant having thermoplastic properties.

The term "implant having thermoplastic properties" refers to any object (e.g. suture anchor or pin) that is suitable for implantation into another object, and having at least partial thermoplastic properties. In other words, the implant comprises a thermoplastic material which imparts thermoplastic properties such that at least a part of the implant can be liquified by the vibrational energy applied to the implant via a sonotrode during implantation, in particular during the insertion of the implant into a recess in a hard tissue (e.g. bone), where the implant will re-solidify due to cooling. Materials having thermoplastic properties suitable for the implant as described herein are known in the art and include, e.g., thermoplastic polymers, e.g.: resorbable or degradable polymers such as polymers based on lactic and/or glycolic acid (PLA, PLLA, PGA, PLGA, PLDLLA, PDLLA etc.) or polyhydroxy alkanoates (PHA), polycaprolactone (PCL), polysaccharides, polydioxanes (PD) polyanhydrides, polypeptides or corresponding copolymers or composite materials (e.g. organic or inorganic fibers or whiskers, e.g. of calcium phosphate ceramics or glasses) containing the named polymers as a component; or non-resorbable or non-degradable polymers such as polyolefines (e.g. polyethylene), polyacrylates, polymetacrylates, polycarbonates, polyamides, polyester, polyurethanes, polysulfones, polyarylketones, polyimides, polyphenyl sulfides or liquid crystal polymers LCPs, polyacetales, halogenated polymers, in particular halogenated polyolefines, polyphenylensulfides, polysulfones, polyethers or equivalent copolymers or composite materials containing the named polymers as a component. For further exemplary thermoplasts, see, e.g., WO 2012/037699, which is incorporated by reference in its entirety, in particular page 6, line 8 to page 9, line 7.

In an embodiment of the device according to the present invention, which may be combined with any of the aspects and embodiments of the device preaddressed or still to be addressed unless in contradiction, the implant is a suture anchor having a suture conduit at the distal end and an opening for inserting a sonotrode at the proximal end, and the implant is positioned in the cavity such that the distal end faces the top opening or inner top opening and the proximal end faces the bottom opening or inner bottom opening. As noted above, the suture conduit can, e.g., be a groove, channel or eyelet.

In an embodiment of the device according to the present invention, which may be combined with any of the aspects and embodiments of the device preaddressed or still to be addressed unless in contradiction, a height of the cavity in direction from the bottom opening to the top opening, or from the inner bottom opening to the inner top opening, corresponds to a length of the implant from the proximal to the distal end. The corresponding lengths are corresponding to the extent that insertion and extraction of the implant from the cavity is still possible, in particular with the aid of a sonotrode.

In an embodiment of the device according to the present invention, which may be combined with any of the aspects and embodiments of the device preaddressed or still to be addressed unless in contradiction, the implant and the housing or inner housing comprise complementary means for positioning the implant in the cavity in a predetermined orientation.

For example, the complementary means for positioning align the slot or the funnel with the suture conduit which can be a groove, channel or eyelet. Alternatively or additionally, the implant may positioned by the complementary means such that the operator using a non-rotationally symmetrical sonotrode can attach the sonotrode without testing different orientations of the sonotrode as explained above.

In an embodiment of the device according to the present invention, which may be combined with any of the aspects and embodiments of the device preaddressed or still to be addressed unless in contradiction, the predetermined orientation relates to an orientation of the implant around an axis from the proximal to the distal end of the implant.

For example, rotating the implant around the axis from the proximal to the distal end can be done to align the slot or the funnel ((inner) top opening) with the suture conduit of the implant which can be a groove, channel or eyelet, or to position the implant such that the operator using a non-rotationally symmetrical sonotrode can attach the sonotrode without testing different orientations.

In an embodiment of the device according to the present invention, which may be combined with any of the aspects and embodiments of the device preaddressed or still to be addressed unless in contradiction, the top opening is a slot or funnel, or the inner and outer top openings are a slot or funnel, the implant is a suture anchor having a suture conduit in the form of a groove or channel, or having a suture conduit in the form of an eyelet, and the predetermined orientation is an alignment of the suture conduit groove or channel with the top opening slot or an alignment of the eyelet with the top opening funnel, or an alignment of the suture conduit groove or channel with the inner and outer top opening slot or an alignment of the eyelet with the inner and outer top opening funnel.

Generally, and as detailed above, the alignment refers to (a) the suture conduit and the slot or funnel to be aligned such that they are essentially in parallel and/or allow or facilitate the attachment of a suture in the suture conduit via the slot or funnel to the suture conduit of the implant in the cavity from outside the housing or outer housing; and to (b) an alignment of the implant such that an operator using a non-rotationally symmetrical sonotrode can attach the sonotrode without testing different orientations of the sonotrode because the implant comprising the complementary recess for the sonotrode is aligned in a known orientation.

In a fifth aspect, the present invention is directed to a kit of parts comprising:

a device according to any of the aspects and embodiments disclosed herein, and an implant of a predefined geometry, wherein the housing or inner housing is configured to position the implant having said predefined geometry in the cavity. The kit of parts optionally further comprises a sonotrode suitable for attachment to the implant. Optionally, the kit of parts further comprises instructions for inserting the implant into the device, for guiding (e.g. attaching) a suture to or from the implant in the device, for attaching a sonotrode to the implant in the device, for extracting the implant from the device and/or general instructions for using the device.

The definitions and explanations provided above in the context of the first, second, third and fourth aspect apply to the fifth aspect unless contradictory or specifically stated otherwise.

In an embodiment of the kit of parts according to the present invention, which may be combined with any of the aspects and embodiments of the kit of parts preaddressed or still to be addressed unless in contradiction, the implant is an implant having thermoplastic properties.

In an embodiment of the kit of parts according to the present invention, which may be combined with any of the aspects and embodiments of the kit of parts preaddressed or still to be addressed unless in contradiction, the implant is a suture anchor, and the kit of parts further comprises at least one of a suture, a needle, or both, wherein the suture is suitable for being attached to the suture anchor.

In a sixth aspect, the present invention is directed to a method of assembling a device according to any of the aspects and embodiments disclosed herein, the method comprising the following steps:

providing a device according to any of the aspects and embodiments disclosed herein, providing an implant of a predefined geometry, in particular a suture anchor, wherein the implant optionally has a distal end and a proximal end, and inserting the implant into the cavity of the device.

The definitions and explanations provided above in the context of the first, second, third, fourth and fifth aspect apply to the sixth aspect unless contradictory or specifically stated otherwise. The implant may, for example, be a suture anchor that already comprises a suture attached to it or a suture anchor that does not comprise a suture.

In an embodiment of the method of assembling a device according to the present invention, which may be combined with any of the aspects and embodiments of the method of assembling a device preaddressed or still to be addressed unless in contradiction, the implant is an implant having thermoplastic properties.

In an embodiment of the method of assembling a device according to the present invention, which may be combined with any of the aspects and embodiments of the method of assembling a device preaddressed or still to be addressed unless in contradiction, the implant is a suture anchor and the method further comprises (a) the step of guiding a suture attached to the suture anchor, in particular attached to a distal end of the suture anchor, from the suture anchor via the top opening or via the inner and outer top openings out from the device, or (b) the step of attaching a suture to the suture anchor, in particular to a distal end of the suture anchor, via the top opening or via the inner and outer top openings.

It is noted that the step of guiding a suture attached to the suture anchor from the suture anchor via the top opening or via the inner and outer top openings out from the device can also be performed while inserting the implant into the cavity of the device.

In an embodiment of the method of assembling a device according to the present invention, which may be combined with any of the aspects and embodiments of the method of assembling a device preaddressed or still to be addressed unless in contradiction, the method further comprises the step attaching a sonotrode to the implant, in particular to a proximal end of the implant, via the bottom opening or via the inner and outer bottom openings.

In an embodiment of the method of assembling a device according to the present invention, which may be combined with any of the aspects and embodiments of the method of assembling a device preaddressed or still to be addressed unless in contradiction, the method further comprises the step of extracting the implant, in particular the implant attached to the sonotrode, from the device.

The step of extracting the implant means that the implant is extracted from the device either via the side opening if it is a device according to the first or second aspect, or is extracted via the bottom opening if it is a device according to the third or fourth aspect.

In a seventh aspect, the present invention is directed to a method of fixating an implant in a recess of an object comprising the steps of:

providing the device according to any of the aspects and embodiments disclosed herein, wherein the implant is an implant having thermoplastic properties, or providing the kit of parts as disclosed herein and inserting the implant into the cavity, or conducting the method of assembling a device as disclosed herein, followed by attaching a sonotrode to the implant via the bottom opening or via the inner and outer bottom openings, extracting the implant attached to the sonotrode from the device, and inserting the implant into a recess of an object, in particular before or while transmitting ultrasound from the sonotrode to the implant for a time sufficient to liquify the implant to the extent that liquefaction results in fixation of the implant in the recess.

The definitions and explanations provided above in the context of the first, second, third, fourth, fifth and sixth aspect apply to the seventh aspect unless contradictory or specifically stated otherwise.

The step of extracting the implant means that the implant is extracted from the device either via the side opening if it is a device according to the first or second aspect, or is extracted via the bottom opening if it is a device according to the third or fourth aspect.

The recess in the object, into which the implant is fixated, can be an elongated recess, e.g. as obtained by drilling with a drill, for example a surgical drill. The recess is drilled to fit the implant or to be slightly smaller (e.g. in cross-section) than the implant but still allows at least partial insertion of the implant.

In an embodiment of the method of fixating an implant in a recess of an object according to the present invention, which may be combined with any of the aspects and embodiments of the method of fixating an implant in a recess of an object preaddressed or still to be addressed unless in contradiction, the implant is a suture anchor, and the method further comprises:

(a) the step of guiding a suture attached to the suture anchor from the suture anchor via the top opening or via the inner and outer top openings out from the device before extracting the implant attached to the sonotrode from the device, or (b) the step of attaching a suture to the suture anchor via the top opening or via the inner and outer top openings before extracting the implant attached to the sonotrode from the device.

In an embodiment of the method of fixating an implant in a recess of an object according to the present invention, which may be combined with any of the aspects and embodiments of the method of fixating an implant in a recess of an object preaddressed or still to be addressed unless in contradiction, the object is a human, animal or artificial hard tissue, a cartilage-covered hard tissue, or an implant structure.

The object, as used herein, can, for example, be a human or animal hard tissue (e.g. bone), a cartilage-covered hard tissue (e.g. cartilage-covered bone), or an implant structure (e.g. fixation plate or bone plate) made, e.g. from titanium, steel, non-resorbable or resorbable polymer material or a fiber composite material. The hard tissue can, for example, be an artificial hard tissue, a hard tissue sample outside of the human or animal body, a hard tissue of a dead body or a hard tissue of a human or animal patient.

In an embodiment of the method of fixating an implant in a recess of an object according to the present invention, which may be combined with any of the aspects and embodiments of the method of fixating an implant in a recess of an object preaddressed or still to be addressed unless in contradiction, at least one of:

the hard tissue is a hard tissue sample outside of the human or animal body, a hard tissue of a dead body or a hard tissue of a patient, and the implant structure is a fixation plate or bone plate.

BRIEF DESCRIPTION OF THE DRAWINGS

Embodiments of the current invention are described in more detail in the following with reference to the figures. These are for illustrative purposes only and are not to be construed as limiting. It is shown in:

FIG. 2A, FIG. 2B, FIG. 2C and FIG. 2D different views of an embodiment of a device for storing an implant;

FIG. 3A, FIG. 3B, FIG. 3C and FIG. 3D an embodiment of a device for storing an implant together with an implant and a sonotrode;

FIG. 4A and FIG. 4B an embodiment of a device for storing an implant with closing means;

DETAILED DESCRIPTION OF THE INVENTION

Figures 1A, 1B, 1C, 1D, 1E:
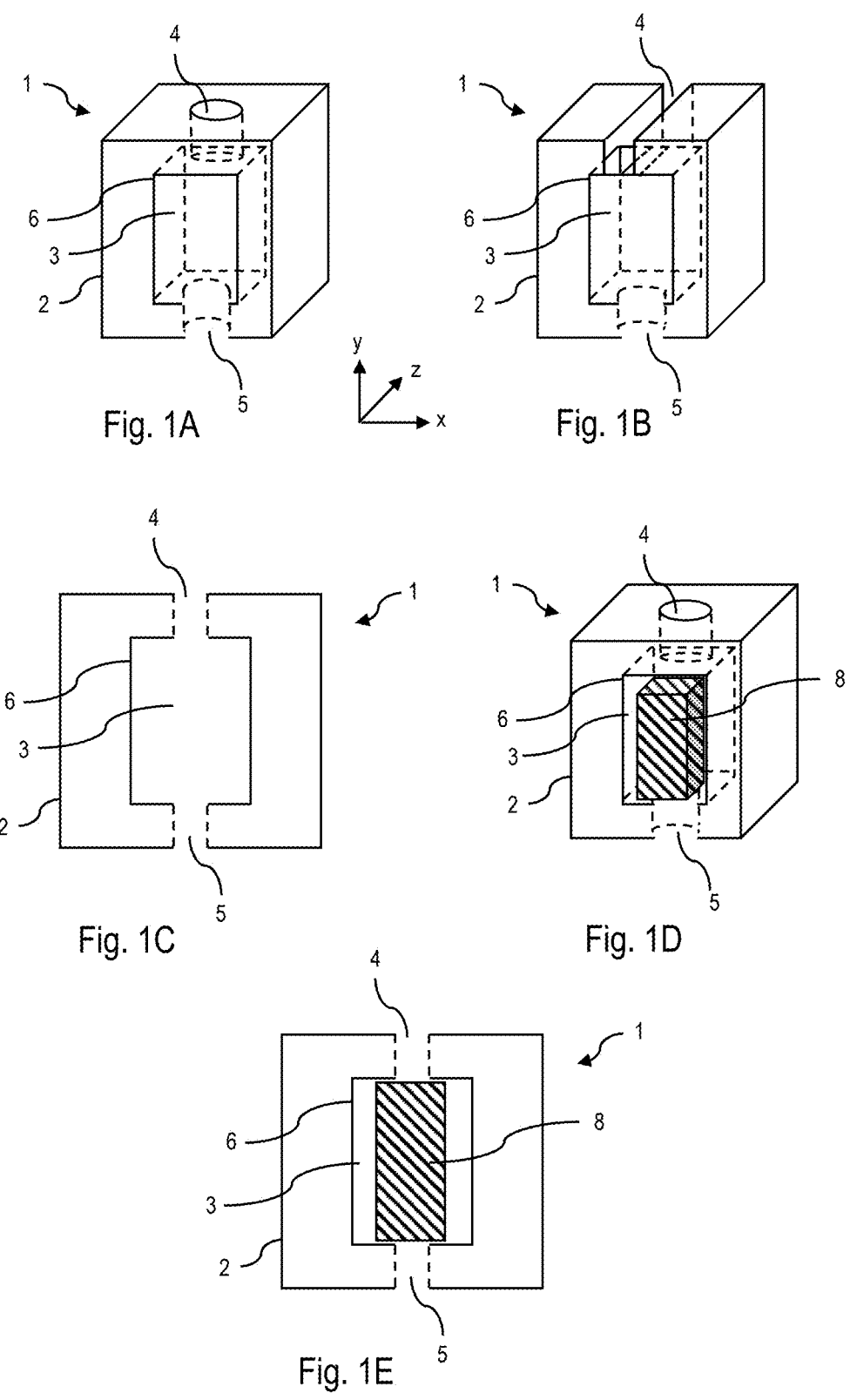
FIG. 1A, FIG. 1B, FIG. 1C, FIG. 1D and FIG. 1E embodiments of a device for storing an implant.

FIG. 1A shows a device 1 for storing an implant, for example according to the first aspect of the present invention. The housing 2 defines a cavity 3 within the housing 2 for receiving and storing an implant (not shown) of a predefined geometry. For example, the cavity 3 is an inner lumen in the housing. The housing 2 comprises a top opening 4 and a bottom opening 5 which are connected to the cavity, i.e. define a passage from outside the housing through the housing to the cavity for guiding (e.g. attaching) a suture to or from an implant in the cavity (top opening) and for attaching a sonotrode to the implant in the cavity (bottom opening). The housing further comprises a side opening 6 for inserting an implant into the cavity and for extracting it therefrom. The side opening may have any size that is suitable for inserting and extracting the implant, it may be smaller than the cavity or have the dimensions of the cavity. The side opening 6 is functionally connected to the bottom opening 5 such that in that an implant stored in the cavity 3 that is attached to a sonotrode via the bottom opening 5 can be extracted via the side opening 6. In the embodiment shown in this Figure, the bottom opening 5 extends in-z direction to form a slot or channel (the functional connection is a structural connection here) so that an implant attached to the sonotrode can be extracted from the cavity 3 via side opening 6 with the sonotrode attached. Generally, the bottom opening 5 can be an incision into the housing 2, e.g. from the surface of the housing that comprises the side opening 6 into the cavity 3 in order to slide or tilt out an implant attached to a sonotrode from the cavity 3. The device 1 is shown as a cuboid for reasons of simplicity but it can have any three-dimensional shape including polyhedrons and spheres. For example, the housing can be polyhedric and the cavity can be spherical, or vice-verso. The words "top" and "bottom" are to be understood as relative terms, in particular relative to the cavity since they are positioned essentially opposite each other with the cavity in between. As shown in FIG. 1B, the top opening 4 can have different shapes, such as a slot. The slot can be particularly suitable for guiding (e.g. attaching) a suture to or from an implant in the cavity because the suture can be aligned with the slot as a guiding structure and, if the suture should be attached, it can be pressed down onto the implant in the cavity. Both, top and bottom openings may have any shape that is suitable for the purpose of guiding (e.g. attaching) a suture and attaching a sonotrode, respectively, with the limitation that they are configured such that an implant having said predefined geometry cannot pass through the top opening and cannot pass through the bottom opening. FIG. 1C shows a cross-sectional (x-y-plane) view of the embodiments of FIGS. 1A and 1B, showing how the top 4 and bottom 5 openings are positioned essentially opposite each other with the cavity 3 positioned in between. FIG. 1D shows an implant 8 stored and positioned in the cavity 3 of the device described in FIG. 1A. The device is configured such that the implant can be inserted and extracted into the cavity 3 via the side opening 6. As shown in this Figure, the top 4 and bottom 5 openings are configured such that the implant 8 having said predefined geometry cannot pass through the top opening and cannot pass through the bottom opening. FIG. 1E shows a cross-sectional (x-y-plane) view of the embodiments of FIG. 1D with the implant 8 stored and positioned in cavity 3.

FIGS. 2A and 2B show different views of an embodiment of the device 1 for storing an implant. In particular, the Figure shows a device 1 according to the first embodiment. The housing 2 comprises a top opening 4 in the form of a slot and a bottom opening 5 in the form of a slot or an incision into the housing 2. In the cavity 3, the housing 2 comprises means for retaining 9 and means for positioning 10 an implant. In this embodiment, the means 9 and 10 protrude into the cavity from the housing 2. An implant can be inserted into cavity 3 via side opening 6 and is then positioned and retained in the cavity by means 9 and 10. In other words, the means 9 and 10 are configured to interact with the implant, for example, to orient a suture conduit in the implant relative to the top opening slot 4. The means for retaining 9 can be shaped as a resilient notch which clips the implant into cavity 3. FIGS. 2C and 2D show different views of the device of FIGS. 2A and 2B with the implant 8 inserted into cavity 3. The means for positioning 10 interact with structural features on the implant 8 to orient the implant, for example as shown in this Figure, such that a suture conduit (the groove at the distal end of the implant 8 facing the top opening 4) aligns with the top opening slot 4.

FIG. 3A shows how a suture 11 and a sonotrode 12 can be attached to the implant 8 stored in the device 1 of FIGS. 2C and 2D. The dotted line shows the alignment of the suture conduit (e.g. a groove) at the distal end of the implant 8 with the top opening slot 4. The proximal end of the implant 8 is positioned such that it is accessible via bottom opening 5 for a sonotrode to be inserted into the implant. Due to the fact that the implant cannot pass through either the top or bottom opening, pressure can be applied to the distal end of the implant when inserting a suture and to the proximal end of the implant when inserting the sonotrode without moving the implant within the housing. The slot 4 can also be suitable for guiding a suture attached to an implant, e.g. a suture anchor, along the slot to keep the suture positioned as desired by an operator. FIGS. 3B, 3C and 3D are shown without the device 1 for easier illustration but they also apply to the implant stored and positioned in the device. FIG. 3B shows the rotation around an axis from the proximal to the distal end of the implant 8 which is controlled by the means for positioning 10 and/or the means for retaining 9 the implant 8 in the cavity 3. FIG. 3C illustrates the suture conduit 13 at the distal end 14 of the implant, and the proximal end 15 at which a sonotrode can be attached to the implant 8. FIG. 3D depicts the sonotrode 12 attached to the proximal end of the implant 8 and the suture 11 attached to the distal end's suture conduit. The implant shown in FIG. 3D corresponds to the implant that can be extracted from the device 1 after attachment of the suture and sonotrode.

FIGS. 4A and 4B show an embodiment of the device 1 for storing an implant, in particular according to the third aspect disclosed herein. The device has a housing 2 which comprises the cavity 3. The implant 8 can be inserted into and extracted from the cavity 3 via the bottom opening 5 (shown open in FIG. 4A). As shown in FIG. 4B, the bottom opening 5 can be closed by closing means 7, for example to protect the implant 8 and/or to prevent the implant from being pushed out of the cavity 3 when a suture is attached to the implant via the top opening 4. The device 1 may also comprise a side opening (slot extending from the top to the bottom opening), however, such a side opening is typically not configured to insert or extract the implant into the cavity 3 because this can be done via bottom opening 5.

Figure 5:
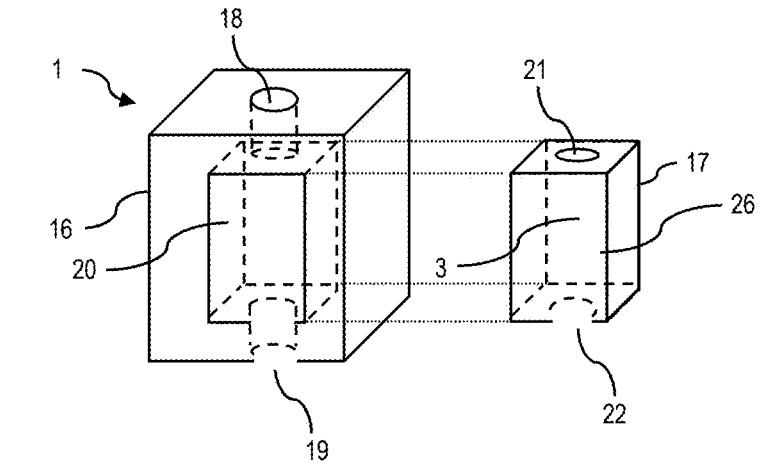
FIG. 5 an embodiment of a device for storing an implant with an outer and inner housing.

FIG. 5 shows an embodiment of a device 1 for storing an implant comprising an outer housing 16 and a removable inner housing 17. The inner housing 16 can be inserted into the outer housing 17 and defines the cavity 3. The top openings 18 and 21, the bottom openings 19 and 22 and side openings 20 and 26 of both, the inner and outer housings, align functionally such that passages into the cavity are formed by these openings which are suitable for the stated purposes (attaching a suture and a sonotrode, inserting and extracting the implant). As detailed in the context of FIGS. 1A to 1D, the side openings 20 and 26 are functionally connected to the bottom openings 19 and 22, for example in that an implant stored in the cavity 3 that is attached to a sonotrode via the bottom openings 19 and 22 can be extracted via the side openings 20 and 26. The outer housing may comprise further side openings which allow for the inner housing to be inserted and extracted.

Figure 6:
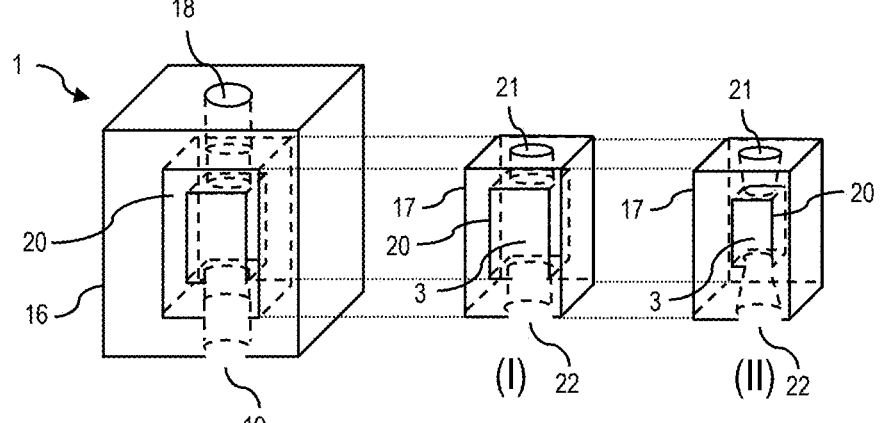
FIG. 6 an embodiment of a device for storing an implant with an outer and inner housing.

FIG. 6 shows an embodiment of a device 1 for storing an implant comprising an outer housing 16 and a removable inner housing 17. In this exemplary embodiment, it is illustrated that different inner housings 17 (I) and 17 (II) can be used in the same outer housing 16. Specifically, the inner housings 17 (I) and (II) differ in the size and optionally shape of their respective cavities 3. In this embodiment, differently sized implants can be inserted into the same outer housing 16 by means of inner housings with differently sized cavities 3 which can adequately store and optionally position the differently sized implants.

Figure 7:
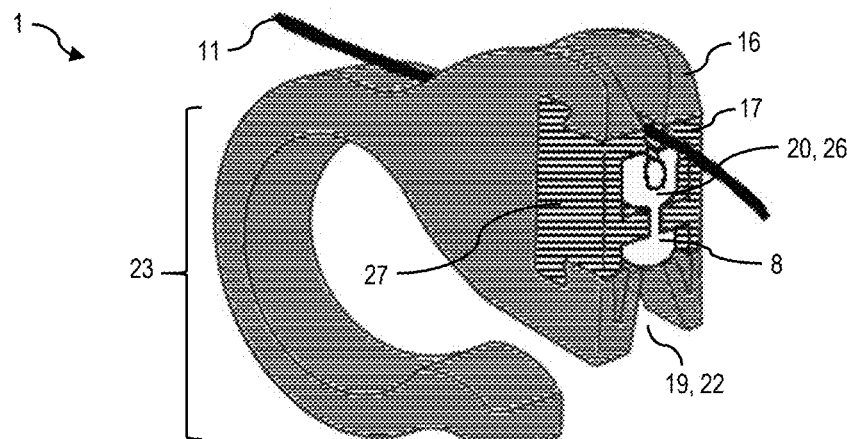
FIG. 7 an embodiment of a device for storing an implant with an outer and inner housing and attachment means.
Figures 8A, 8B, 8C, 8D:
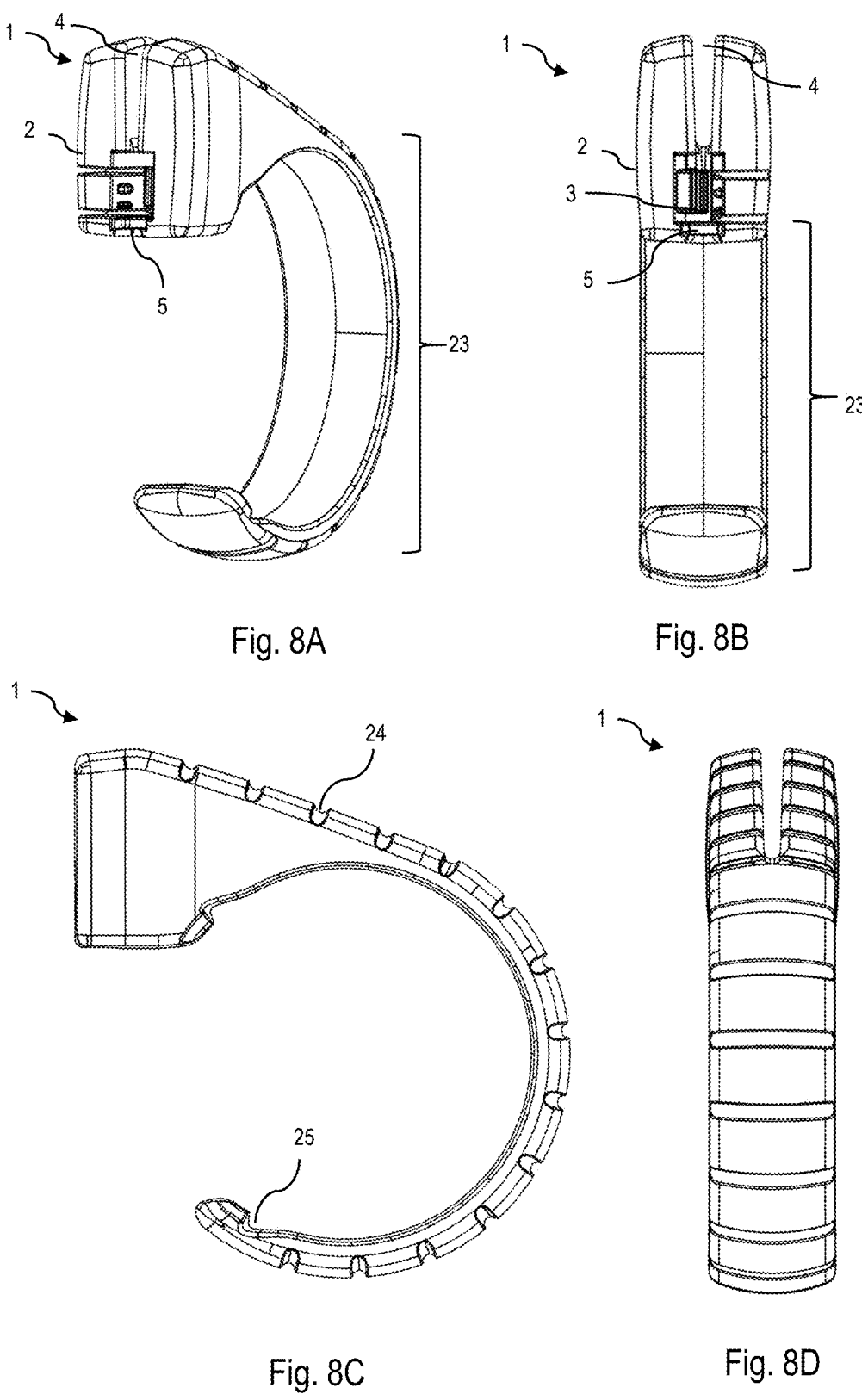
FIG. 8A, FIG. 8B, FIG. 8C and FIG. 8D different views of an embodiment of a device for storing an implant with attachment means.

FIG. 7 shows a specific embodiment of a device 1 for storing an implant comprising an outer housing 16 and a removable inner housing 17. The side openings 20 and 26 are functionally connected to the bottom openings 19 and 22, such that the implant 8 stored in the cavity 3 can be extracted (e.g. by tilting) via the side openings 20 and 26 when the implant is attached to a sonotrode via the bottom openings 19 and 22. A suture 11 can be attached to the implant via the top openings (not labelled, here in the form of a slot) in the outer housing 16 and inner housing 17. As shown in this example, the outer housing 16 comprises two further side openings 27 (only one labelled, the other one is opposite the labelled one) which are configured for inserting and extracting the inner housing 17. The device further comprises attachment means 23 on the outer housing 16 for attaching the device to a sonotrode apparatus.

FIGS. 8A, 8B, 8C and 8D show different views of the device 1 of FIGS. 2A-2D and 3A-3D further comprising attachment means 23 on the housing 2 for attaching the device to a sonotrode apparatus. The attachment means 23 can be (partly) circular to be attached to a sonotrode or a handheld thereof by clipping the attachment means around the sonotrode or handheld. The attachment means 23 may further comprise grooves, mounting means or guiding means 24, e.g. for mounting a needle or for guiding or mounting a suture. The grooves 24 may further impart flexibility on the attachment means 23. Additionally, the attachment means 23 may comprise a guiding or mounting notch 25, which forms a hollow passage between the attachment means and a handheld when the device is clipped onto a handheld with the attachment means. The guiding or mounting notch 25 can serve for guiding a suture, e.g. during implantation of a suture anchor to which the suture is attached.

REFERENCE SIGNS LIST

1 Device for storing implant
2 Housing
3 Cavity
4 Top opening
5 Bottom opening
6 Side opening
7 Closing means
8 Implant
9 Means for retaining
10 Means for positioning
11 Suture
12 Sonotrode
13 Suture conduit
14 Distal end of implant
15 Proximal end of implant
16 Outer housing
17 Inner housing
18 Outer top opening
19 Outer bottom opening
20 Outer side opening
21 Inner top opening
22 Inner bottom opening
23 Attachment means
24 Groove or mounting means
25 Guiding or mounting notch
26 Inner side opening
27 Further side opening

The invention claimed is:

1. A device for storing an implant comprising a housing defining a cavity suitable for receiving and storing an implant of a predefined geometry, wherein the housing comprises:

a top opening for guiding a suture to or from an implant stored in the cavity, a bottom opening for attaching a sonotrode to an implant stored in the cavity, and a side opening for inserting and extracting an implant into and from the cavity, wherein the bottom opening is functionally connected to the side opening, the cavity is located between the top and bottom openings, the housing is configured to position an implant having said predefined geometry in the cavity such that a suture can be guided to or from the implant via the top opening and a sonotrode can be attached via the bottom opening to the implant, and the top and bottom openings are positioned essentially opposite each other and are configured such that an implant having said predefined geometry cannot pass through the top opening and cannot pass through the bottom opening.

2. The device according to claim 1, wherein the housing comprises at least one of:

means for retaining an implant in the cavity, means for positioning an implant in the cavity in a predetermined position, or both.

3. The device according to claim 2, wherein at least one of the means for retaining the implant in the cavity, the means for positioning the implant in the cavity, or both, extend into the cavity.

4. The device according to claim 2, wherein at least one of the means for retaining the implant in the cavity, the means for positioning the implant in the cavity, or both, are clamping means for retaining the implant in the cavity.

5. The device according to claim 1, wherein the top opening is a slot or a funnel.

6. The device according to claim 5, wherein the housing comprises means for positioning an implant in the cavity such that a suture conduit in the implant aligns with the slot or funnel in the top opening of the housing, and that a suture can be guided from the suture conduit or inserted into the suture conduit via the slot or funnel.

7. The device according to claim 1, further comprising attachment means on the device or on the housing for attaching the device to a sonotrode apparatus.

8. The device according to claim 7, wherein the attachment means further comprise at least one of:

mounting means for a needle, mounting means for a suture, or both.

9. The device according to claim 1, wherein the top and bottom openings are dimensioned such that an implant having said predefined geometry cannot pass through the top opening and the bottom opening, or the top and bottom openings comprise means for preventing an implant having said predefined geometry to pass through the top opening and the bottom opening.

10. The device according to claim 1, wherein the device comprises an implant of a predefined geometry having a distal end and a proximal end in the cavity.

11. The device according to claim 10, wherein the implant is an implant having thermoplastic properties.

12. The device according to claim 10, wherein the implant is a suture anchor having a suture conduit at the distal end and an opening for inserting a sonotrode at the proximal end, and the implant is positioned in the cavity such that the distal end faces the top opening and the proximal end faces the bottom opening.

13. The device according to claim 10, wherein a height of the cavity in direction from the bottom opening to the top opening, corresponds to a length of the implant from the proximal to the distal end.

14. The device according to claim 10, wherein the implant and the housing comprise complementary means for positioning the implant in the cavity in a predetermined orientation.

15. The device according to claim 14, wherein the predetermined orientation relates to an orientation of the implant around an axis from the proximal to the distal end of the implant.

16. The device according to claim 14, wherein
the top opening is a slot or funnel,
the implant is a suture anchor having a suture conduit in a form of a groove or channel, or having a suture conduit in a form of an eyelet, and
the predetermined orientation is an alignment of the suture conduit groove or channel with the top opening slot or an alignment of the eyelet with the top opening funnel.

17. A kit of parts comprising:
a device according to claim 1, and an implant of a predefined geometry, wherein the housing is configured to position the implant having said predefined geometry in the cavity.

18. The kit of parts according to claim 17, wherein the implant is an implant having thermoplastic properties.

19. The kit of parts according to claim 17, wherein the implant is a suture anchor, and the kit of parts further comprises at least one of a suture, a needle, or both, wherein the suture is suitable for being attached to the suture anchor.

20. The device according to claim 1, wherein the top and bottom openings are structurally shaped or dimensioned such that the implant having said predefined geometry is prevented from passing through the top and bottom openings, and
wherein the bottom opening and the side opening are connected such that the implant can be extracted from the cavity via the side opening while being attached to the sonotrode that is attached to the implant via the bottom opening.

21. A device for storing an implant comprising an outer housing and a removable inner housing,
wherein the outer housing comprises:
an outer top opening for guiding a suture to or from an implant stored in the inner housing,
an outer bottom opening for attaching a sonotrode to an implant stored in the inner housing, and
at least one outer side opening, and
the inner housing,
wherein the inner housing defines a cavity suitable for receiving and storing an implant of a predefined geometry, and comprises:
an inner top opening functionally connected to the outer top opening,
an inner bottom opening functionally connected to the outer bottom opening, and
an inner side opening functionally connected to the at least one outer side opening for inserting and extracting an implant into and from the cavity,
wherein
the inner and outer bottom openings are functionally connected to at least one outer side opening and the inner side opening,
the cavity is located between the inner top and inner bottom openings,
the inner housing is configured to position an implant having said predefined geometry in the cavity such that a suture can be guided to or from the implant via the outer and inner top opening and a sonotrode can be attached via the outer and inner bottom opening to the implant, and
the inner top and inner bottom openings, and the outer top and outer bottom openings are positioned essentially opposite each other and are configured such that an implant having said predefined geometry cannot pass through at least one of the inner top opening, the outer top opening, or both, and cannot pass through at least one of the inner bottom opening, the outer bottom opening, or both.

22. A device for storing an implant comprising a housing defining a cavity suitable for receiving and storing an implant of a predefined geometry, wherein the housing comprises:
a top opening for guiding a suture to or from an implant stored in the cavity,
a bottom opening for inserting and extracting an implant of a predefined geometry, and for attaching a sonotrode to an implant stored in the cavity, and
closing means for closing the bottom opening,
wherein
the cavity is located between the top and bottom openings,
the housing is configured to position an implant having said predefined geometry in the cavity such that a suture can be guided to or from the implant via the top opening and a sonotrode can be attached via the bottom opening to the implant,
the top and bottom openings are positioned essentially opposite each other, and
the top opening is configured such that an implant having said predefined geometry cannot pass through the top opening.

23. A device for storing an implant comprising an outer housing and a removable inner housing,
wherein the outer housing comprises:
an outer top opening for guiding a suture to or from an implant stored in the inner housing,
an outer bottom opening for inserting and extracting the inner housing, and for attaching a sonotrode to an implant stored in the inner housing,
closing means for closing the outer bottom opening, and
the inner housing,
wherein the inner housing defines a cavity suitable for receiving and storing an implant of a predefined geometry, and comprises:
an inner top opening functionally connected to the outer top opening,
an inner bottom opening functionally connected to the outer bottom opening,
wherein
the cavity is located between the inner top and inner bottom openings,
the inner housing is configured to position an implant having said predefined geometry in the cavity such that a suture can be guided to or from the implant via the outer and inner top opening and a sonotrode can be attached via the outer and inner bottom opening to the implant, and
the inner top and inner bottom openings are positioned essentially opposite each other, and
at least one of the inner top opening, the outer top opening, or both, is configured such that an implant having said predefined geometry cannot pass through at least one of the inner top opening, the outer top opening, or both.

24. A method of assembling a device comprising:
providing a device for storing an implant comprising an outer housing and a removable inner housing, wherein the outer housing comprises an outer top opening for guiding a suture to or from an implant stored in the inner housing, an outer bottom opening for attaching a sonotrode to an implant stored in the inner housing, and at least one outer side opening, and the inner housing, wherein the inner housing defines a cavity suitable for receiving and storing an implant of a predefined geometry, and comprises an inner top opening functionally connected to the outer top opening, an inner bottom opening functionally connected to the outer bottom opening, and an inner side opening functionally connected to the at least one outer side opening for inserting and extracting an implant into and from the cavity, wherein the inner and outer bottom openings are functionally connected to at least one outer side opening and the inner side opening, the cavity is located between the inner top and inner bottom openings, the inner housing is configured to position an implant having said predefined geometry in the cavity such that a suture can be guided to or from the implant via the outer and inner top opening and a sonotrode can be attached via the outer and inner bottom opening to the implant, and the inner top and inner bottom openings, and the outer top and outer bottom openings are positioned essentially opposite each other and are configured such that an implant having said predefined geometry cannot pass through at least one of the inner top opening, the outer top opening, or both, and cannot pass through at least one of the inner bottom opening, the outer bottom opening, or both, providing an implant of a predefined geometry having a distal end and a proximal end, and inserting the implant into the cavity of the device.

25. A method of fixating an implant in a recess of an object comprising:

providing a device for storing an implant comprising an outer housing and a removable inner housing, wherein the outer housing comprises an outer top opening for guiding a suture to or from an implant stored in the inner housing, an outer bottom opening for attaching a sonotrode to an implant stored in the inner housing, and at least one outer side opening, and the inner housing, wherein the inner housing defines a cavity suitable for receiving and storing an implant of a predefined geometry, and comprises an inner top opening functionally connected to the outer top opening, an inner bottom opening functionally connected to the outer bottom opening, and an inner side opening functionally connected to the at least one outer side opening for inserting and extracting an implant into and from the cavity, wherein the inner and outer bottom openings are functionally connected to at least one outer side opening and the inner side opening, the cavity is located between the inner top and inner bottom openings, the inner housing is configured to position an implant having said predefined geometry in the cavity such that a suture can be guided to or from the implant via the outer and inner top opening and a sonotrode can be attached via the outer and inner bottom opening to the implant, and the inner top and inner bottom openings, and the outer top and outer bottom openings are positioned essentially opposite each other and are configured such that an implant having said predefined geometry cannot pass through at least one of the inner top opening, the outer top opening, or both, and cannot pass through at least one of the inner bottom opening, the outer bottom opening, or both, wherein the device comprises an implant of a predefined geometry having a distal end and a proximal end in the cavity and wherein the implant is an implant having thermoplastic properties, attaching a sonotrode to the implant via the inner bottom opening or via the inner and outer bottom openings, extracting the implant attached to the sonotrode from the device, and inserting the implant into a recess of an object, while or before transmitting ultrasound from the sonotrode to the implant for a time sufficient to liquify the implant to an extent that liquefaction results in fixation of the implant in the recess.

26. A method of fixating an implant in a recess of an object, the method comprising:

providing a device for storing an implant comprising a housing defining a cavity suitable for receiving and storing an implant of a predefined geometry, wherein the housing comprises:

a top opening for guiding a suture to or from an implant stored in the cavity, a bottom opening for attaching a sonotrode to an implant stored in the cavity, and a side opening for inserting and extracting an implant into and from the cavity, wherein the bottom opening is functionally connected to the side opening, the cavity is located between the top and bottom openings, the housing is configured to position an implant having said predefined geometry in the cavity such that a suture can be guided to or from the implant via the top opening and a sonotrode can be attached via the bottom opening to the implant, and the top and bottom openings are positioned essentially opposite each other and are configured such that an implant having said predefined geometry cannot pass through the top opening and cannot pass through the bottom opening;

providing an implant of a predefined geometry having a distal end and a proximal end, and inserting the implant into the cavity of the device.

27. The method according to claim 26, wherein the implant is an implant having thermoplastic properties.

28. The method according to claim 26, wherein the implant is a suture anchor and the method further comprises:

(a) a step of guiding a suture attached to the suture anchor from the suture anchor via the top opening out from the device, or (b) a step of attaching a suture to the suture anchor via the top opening.

29. The method according to claim 26, wherein the method further comprises a step of attaching a sonotrode to the implant via the bottom opening.

30. The method according to claim 29, wherein the method further comprises a step of extracting the implant attached to the sonotrode from the device.

31. A method of fixating an implant in a recess of an object, the method comprising the steps of:

providing a device for storing an implant comprising a housing defining a cavity suitable for receiving and storing an implant of a predefined geometry, wherein the housing comprises:

a top opening for guiding a suture to or from an implant stored in the cavity, a bottom opening for attaching a sonotrode to an implant stored in the cavity, and a side opening for inserting and extracting an implant into and from the cavity, wherein the bottom opening is functionally connected to the side opening, the cavity is located between the top and bottom openings, the housing is configured to position an implant having said predefined geometry in the cavity such that a suture can be guided to or from the implant via the top opening and a sonotrode can be attached via the bottom opening to the implant, and the top and bottom openings are positioned essentially opposite each other and are configured such that an implant having said predefined geometry cannot pass through the top opening and cannot pass through the bottom opening;

wherein the device comprises an implant of a predefined geometry having a distal end and a proximal end in the cavity;

attaching a sonotrode to the implant via the bottom opening, extracting the implant attached to the sonotrode from the device, and inserting the implant into a recess of an object while or before transmitting ultrasound from the sonotrode to the implant for a time sufficient to liquify the implant to an extent that liquefaction results in fixation of the implant in the recess.

32. The method according to claim 31, wherein the implant is a suture anchor, and the method further comprises:

(a) a step of guiding a suture attached to the suture anchor from the suture anchor via the top opening out from the device before extracting the implant attached to the sonotrode from the device, or (b) a step of attaching a suture to the suture anchor via the top opening before extracting the implant attached to the sonotrode from the device.

33. The method according to claim 31, wherein the object is a human, animal or artificial hard tissue, a cartilage-covered hard tissue, or an implant structure.

34. The method according to claim 33, wherein at least one of:

the hard tissue is a hard tissue sample outside of a human or animal body, a hard tissue of a dead body or a hard tissue of a patient, and the implant structure is a fixation plate or bone plate.

\* \* \* \* \*